(12) United States Patent
Melkent et al.

(10) Patent No.: US 9,895,235 B2
(45) Date of Patent: Feb. 20, 2018

(54) SPINAL IMPLANT SYSTEM AND METHOD

(71) Applicant: Warsaw Orthopedic, Inc., Warsaw, IN (US)

(72) Inventors: Anthony J. Melkent, Germantown, TN (US); Jonathan E. Blackwell, Arlington, TN (US); Cristian A. Capote, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 38 days.

(21) Appl. No.: 14/974,685

(22) Filed: Dec. 18, 2015

(65) Prior Publication Data
US 2017/0172757 A1 Jun. 22, 2017

(51) Int. Cl.
*A61F 2/44* (2006.01)
*A61F 2/46* (2006.01)
*A61F 2/28* (2006.01)
*A61F 2/30* (2006.01)

(52) U.S. Cl.
CPC .......... *A61F 2/4455* (2013.01); *A61F 2/4611* (2013.01); *A61F 2002/2835* (2013.01); *A61F 2002/3082* (2013.01); *A61F 2002/30622* (2013.01); *A61F 2002/30836* (2013.01); *A61F 2002/30841* (2013.01); *A61F 2002/4475* (2013.01); *A61F 2002/4615* (2013.01)

(58) Field of Classification Search
CPC .................. A61F 2/4611; A61F 2/4455; A61F 2002/2835
See application file for complete search history.

(56) References Cited

U.S. PATENT DOCUMENTS

| | | | |
|---|---|---|---|
| 9,445,918 B1* | 9/2016 | Lin | A61B 17/8819 |
| 2007/0255416 A1* | 11/2007 | Melkent | A61F 2/4465 |
| | | | 623/17.16 |
| 2011/0137421 A1* | 6/2011 | Hansell | A61F 2/4425 |
| | | | 623/17.16 |
| 2012/0078373 A1* | 3/2012 | Gamache | A61B 17/8625 |
| | | | 623/17.16 |
| 2012/0143336 A1* | 6/2012 | Aflatoon | A61F 2/4465 |
| | | | 623/17.16 |
| 2014/0039622 A1* | 2/2014 | Glerum | A61F 2/442 |
| | | | 623/17.15 |
| 2014/0172105 A1* | 6/2014 | Frasier | A61F 2/4611 |
| | | | 623/17.16 |
| 2015/0100126 A1* | 4/2015 | Melkent | A61F 2/4455 |
| | | | 623/17.16 |
| 2015/0100128 A1* | 4/2015 | Glerum | A61F 2/447 |
| | | | 623/17.16 |

(Continued)

*Primary Examiner* — Ellen C Hammond
*Assistant Examiner* — Stuart S Bray

(57) ABSTRACT

A spinal implant comprises an implant body extending between an anterior surface and a posterior surface, and including a first vertebral engaging surface and a second vertebral engaging surface. The implant body includes an inner surface that defines at least one opening oriented to implant a fastener oblique relative to a lateral axis of a subject body and adjacent an intervertebral space of the subject body. The implant body defining a cavity such that a surgical instrument is connectable with the implant body adjacent the cavity and movable relative to the implant body. Systems, surgical instruments and methods are disclosed.

20 Claims, 9 Drawing Sheets

(56) References Cited

U.S. PATENT DOCUMENTS

| | | | |
|---|---|---|---|
| 2015/0100129 A1* | 4/2015 | Waugh | A61F 2/4455 623/17.16 |
| 2015/0250607 A1* | 9/2015 | Drochner | A61F 2/4455 623/17.16 |
| 2016/0120660 A1* | 5/2016 | Melkent | A61F 2/4455 623/17.16 |
| 2016/0287236 A1* | 10/2016 | Garcia-Bengochea | A61B 17/0206 |
| 2017/0014240 A1* | 1/2017 | Seifert | A61F 2/447 |
| 2017/0014244 A1* | 1/2017 | Seifert | A61F 2/4455 |
| 2017/0095240 A9* | 4/2017 | Waugh | A61B 17/025 |
| 2017/0095342 A9* | 4/2017 | Waugh | A61F 2/442 |

* cited by examiner

SPINAL IMPLANT SYSTEM AND METHOD

TECHNICAL FIELD

The present disclosure generally relates to medical devices for the treatment of musculoskeletal disorders, and more particularly to a spinal implant system and a method for treating a spine.

BACKGROUND

Spinal pathologies and disorders such as degenerative disc disease, disc herniation, spondylolisthesis, stenosis, osteoporosis, tumor, scoliosis and other curvature abnormalities, kyphosis and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, correction, discectomy, microdiscectomy, corpectomy, decompression, laminectomy, laminotomy, foraminotomy, facetectomy and implantable prosthetics. As part of these surgical treatments, spinal constructs, such as, for example, bone fasteners, spinal rods and interbody devices can be used to provide stability to a treated region. For example, during surgical treatment, surgical instruments can be used to deliver components of the spinal constructs to the surgical site for fixation with bone to immobilize a joint. Certain spinal surgery approaches utilize a direct lateral approach to access intervertebral spaces, however, these techniques present certain challenges due to the location of musculature and neural structures embedded therein. This disclosure describes an improvement over these prior technologies.

SUMMARY

In one embodiment, a spinal implant comprises an implant body extending between an anterior surface and a posterior surface, and including a first vertebral engaging surface and a second vertebral engaging surface. The implant body includes an inner surface that defines at least one opening oriented to implant a fastener oblique relative to a lateral axis of a subject body and adjacent an intervertebral space of the subject body. The implant body defining a cavity such that a surgical instrument is connectable with the implant body adjacent the cavity and movable relative to the implant body. In some embodiments, systems, surgical instruments and methods are provided.

BRIEF DESCRIPTION OF THE DRAWINGS

The present disclosure will become more readily apparent from the specific description accompanied by the following drawings, in which.

DETAILED DESCRIPTION

Figure 1:
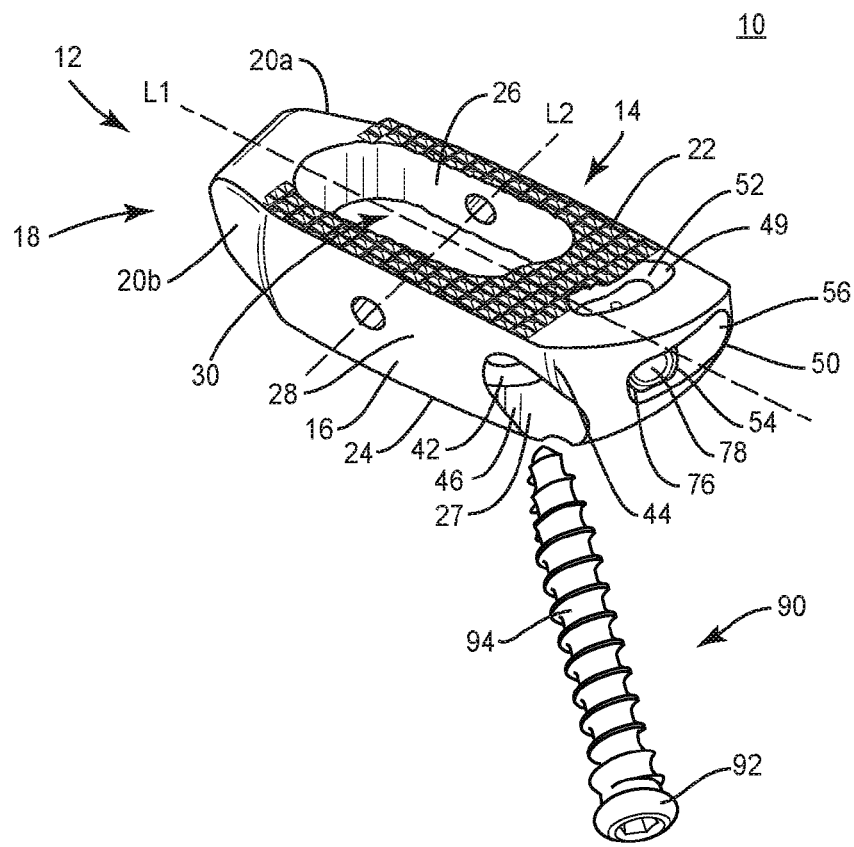
FIG. 1 is a perspective view of components of one embodiment of a surgical system in accordance with the principles of the present disclosure.

The exemplary embodiments of the surgical system and related methods of use disclosed are discussed in terms of medical devices for the treatment of musculoskeletal disorders and more particularly, in terms of a surgical system for implant delivery to a surgical site and a method for treating a spine. In some embodiments, the systems and methods of the present disclosure employ an oblique surgical pathway, which may include an oblique-lateral surgical pathway. In some embodiments, the systems and methods of the present disclosure are employed with a spinal joint and fusion, for example, with a cervical, thoracic, lumbar and/or sacral region of a spine.

In some embodiments, the surgical system includes an interbody implant configured as a stand-alone device. In some embodiments, the interbody implant can be employed with a method for lordotic correction. In some embodiments, the interbody implant is configured for insertion along an oblique pathway. In some embodiments, the interbody implant includes an oblique opening, such as, for example, a screw hole configured for disposal of a bone screw. In some embodiments, the oblique opening is configured to facilitate fixation of a bone fastener obliquely into and through the interbody implant and into an adjacent vertebral body endplate.

In some embodiments, the surgical system is employed with a method for treating a spine that includes the step of creating additional lordosis using the interbody implant. In some embodiments, the interbody implant includes an oblique lateral shape. In some embodiments, the interbody implant includes a slidable inserter aperture.

In some embodiments, the surgical system includes an interbody implant employed with a method of anterior posterior lordotic correction of vertebrae. In some embodiments, the method includes the step of treating vertebrae including a first vertebral surface and a second vertebral surface, the vertebral surfaces being disposed at a relative lordotic angle of approximately 5 angular degrees. In some embodiments, the method includes the step of removing vertebral tissue from between and/or including the vertebral surfaces. In some embodiments, the vertebrae defines a disc space between the vertebral surfaces and the method includes the step of inserting an interbody implant into the disc space. In some embodiments, the method includes the step of aligning an upper surface of the interbody implant into a flush orientation with a first vertebral surface. In some embodiments, the method includes the step of inserting a bone fastener through the interbody implant and into the first vertebral surface to lock the interbody implant into position with the vertebrae such that an angular gap is defined between the interbody implant and a second vertebral surface. In some embodiments, the method includes the step of removing posterior bone to facilitate angular correction. In some embodiments, the method includes the step of removing facet joints. In some embodiments, the method includes the step of removing a portion of a lamina. In some embodiments, the method includes the step of removing a portion of a spinous process.

In some embodiments, the method includes the step of manipulating the vertebral surfaces to reduce and/or rotate the vertebral surfaces such that a lower surface of the interbody implant is flush with the second vertebral surface. In some embodiments, the method includes the step of manipulating the vertebral surfaces to a relative lordotic angle of approximately 20 angular degrees. In some embodiments, the step of manipulating includes utilizing instruments, external manipulation or posterior fixation devices, such as, for example, pedicle screws, to reduce and/or rotate the vertebral surfaces. In some embodiments, the method includes the step of locking the vertebral surfaces at a relative lordotic angle orientation with posterior implants, such as, for example, bi-lateral pedicle screws and spinal rods.

In some embodiments, the surgical system includes an interbody implant employed with a method that includes an oblique lateral interbody fusion (OLIF) procedure. In some embodiments, the surgical system includes a surgical instrument, such as, for example, an inserter configured for connection with an interbody implant. In some embodiments, the inserter can be attached with the interbody implant in-line, at various oblique angles and/or modified inter-operatively.

In some embodiments, the interbody implant is configured for connection with a single bone fastener. In some embodiments, the interbody implant is configured for connection with multiple bone fasteners. In some embodiments, the multiple bone fasteners are configured for fixation with only one vertebral endplate.

In some embodiments, the surgical system includes an interbody implant employed with a method of treating a spine, which includes the step of inserting the interbody implant into a patient when a patient is disposed in a lateral position with the left side up and the bone fastener is connected with a superior vertebral endplate. In some embodiments, the surgical system includes an interbody implant employed with a method of treating a spine, which includes the step of inserting the interbody implant into a patient when a patient is disposed in a lateral position with the right side up and the bone fastener is connected with an inferior vertebral endplate. In some embodiments, the surgical system includes an interbody implant employed with a method of treating a spine, which includes the step of inserting the interbody implant into a patient when a patient is disposed in a lateral position with the left side up and the bone fastener is connected with an inferior vertebral endplate. In some embodiments, the surgical system includes an interbody implant employed with a method of treating a spine, which includes the step of inserting the interbody implant into a patient when a patient is disposed in a lateral position with the right side up and the bone fastener is connected with a superior vertebral endplate.

In some embodiments, the surgical system includes an interbody implant employed with a method of treating a spine, which includes the step of providing posterior fixation with pedicle screws and spinal rods. In some embodiments, posterior fixation can include other implants, such as, for example, facet screws and/or spinous process plates.

In some embodiments, the surgical system includes an interbody implant employed with a method of treating a spine, which includes the step of providing an interbody implant having one or more openings configured for disposal of bone fasteners for connection with vertebrae having a first vertebral surface, such as, for example, a first vertebral endplate and a second vertebral surface, such as, for example, a second vertebral endplate. In some embodiments, the method includes the step of fixing the interbody implant with the first vertebral endplate from a lateral approach or an anterior approach. In some embodiments, the method includes the step of manipulating the vertebrae for posterior correction via a posterior approach with or without permanent posterior fixation attached. In some embodiments, the method includes the step of fixing the interbody implant with the second vertebral endplate from a lateral or anterior approach.

In some embodiments, the surgical system is used with surgical navigation, such as, for example, fluoroscope or image guidance. In some embodiments, one or all of the components of the surgical system are disposable, peel-pack, pre-packed sterile devices. One or all of the components of the surgical system may be reusable. The surgical system may be configured as a kit with multiple sized and configured components.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. The present disclosure may also be alternatively employed with procedures for treating the lumbar, cervical, thoracic, sacral and pelvic regions of a spinal column. The system and methods of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. As used in the specification and including the appended claims, the term "tissue" includes soft tissue, ligaments, tendons, cartilage and/or bone unless specifically referred to otherwise.

Figure 2:
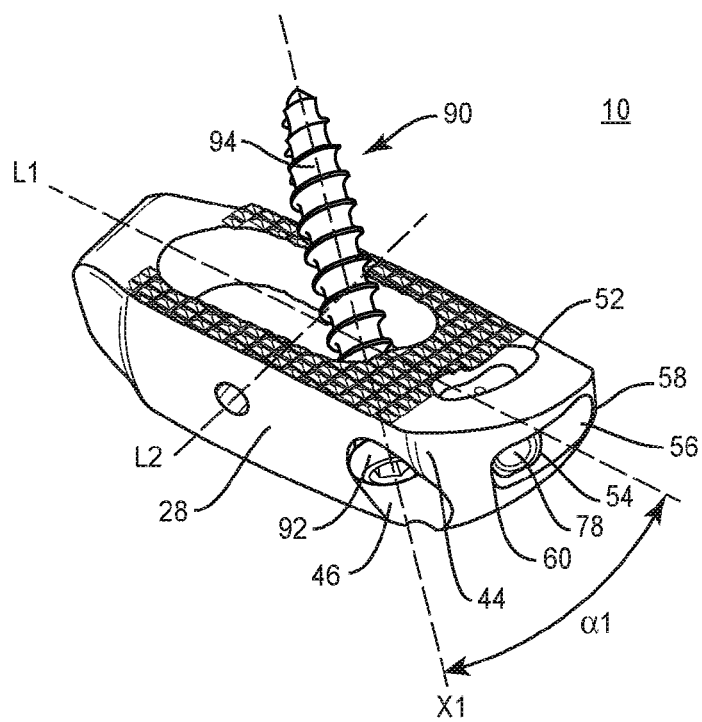
FIG. 2 is a perspective view of the components shown in FIG. 1.

The following discussion includes a description of a surgical system and related methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1 and 2, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate such as hydroxyapatite (HA), corraline HA, biphasic calcium phosphate, tricalcium phosphate, or fluorapatite, tri-calcium phosphate (TCP), HA-TCP, calcium sulfate, or other resorbable polymers such as polyaetide, polyglycolide, polytyrosine carbonate, polycaroplaetohe and their combinations, biocompatible ceramics, mineralized collagen, bioactive glasses, porous metals, bone particles, bone fibers, morselized bone chips, bone morphogenetic proteins (BMP), such as BMP-2, BMP-4, BMP-7, rhBMP-2, or rhBMP-7, demineralized bone matrix (DBM), transforming growth factors (TGF, e.g., TGF-β), osteoblast cells, growth and differentiation factor (GDF), insulin-like growth factor 1, platelet-derived growth factor, fibroblast growth factor, or any combination thereof.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 is employed, for example, with a fully open surgical procedure, a minimally invasive procedure, including percutaneous techniques, and mini-open surgical techniques to deliver and introduce instrumentation and/or an implant, such as, for example, an interbody implant, at a surgical site of a patient, which includes, for example, a spine having vertebrae V, as shown in FIGS. 5-16. In some embodiments, a surgical pathway P to a surgical site is formed via an OLIF or OLIF procedure. In some embodiments, the implant can include spinal constructs, such as, for example, bone fasteners, spinal rods, connectors and/or plates.

Figure 8:
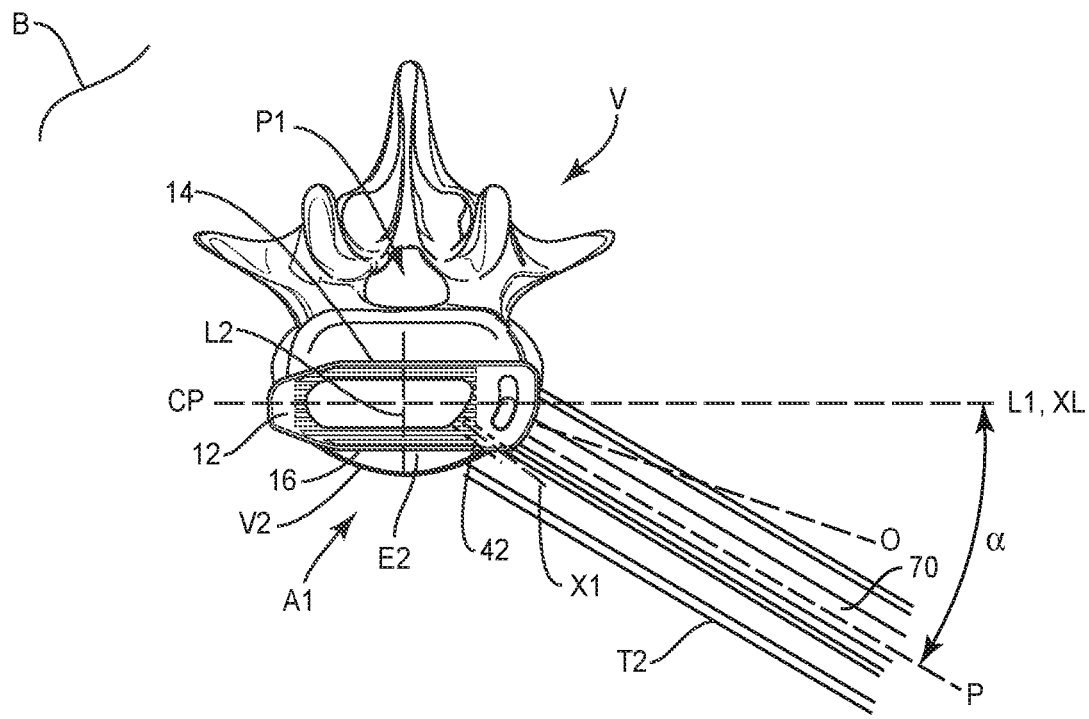
FIG. 8 is an axial view of components of one embodiment of a surgical system in accordance with the principles of the present disclosure disposed with vertebrae.

Spinal implant system 10 includes an implant body, such as, for example, an interbody cage 12, as shown in FIGS. 1 and 2. Cage 12 extends between a posterior surface 14 and an anterior surface 16 and defines an axis L1. Posterior surface 14 is configured to face a posterior side of a subject body B (FIG. 8) and be disposed adjacent an posterior portion of vertebrae, such as, for example a posterior portion P1 of one or more intervertebral spaces of vertebrae V (FIG. 8). Anterior surface 16 is configured to face an anterior side of subject body B and be disposed adjacent an anterior portion of vertebrae, such as, for example an anterior portion A1 of one or more intervertebral spaces of vertebrae V (FIG. 8).

In some embodiments, cage 12 includes a convex distal end, such as, for example, a bullet nose 18 to facilitate insertion by a surgeon. In some embodiments, cage 12 may include chamfers, such as, for example, cut outs 20a, 20b disposed on bullet nose 18 such that cage 12 may be placed in an intervertebral space to avoid impinging on various structures in or near vertebral tissue, such as, for example, a spinal foramina.

In some embodiments, cage 12 includes any number and configuration of radiopaque markers (such as tantalum pins (not shown)) for visualizing a position of cage 12 using fluoroscopy during insertion, manipulation and implantation. In some embodiments, the markers may be placed obliquely on bullet nose 18, in sidewalls of cage 12 adjacent surfaces 14, 16 and/or in a proximal end of cage 12. In some embodiments, the markers may be placed parallel, oblique to and/or perpendicular to surfaces 14, 16 as required to properly visualize the position of cage 12 relative to a surgical pathway P and/or relative to an oblique axis O (FIG. 8) to facilitate placement of cage 12, as described herein.

Figure 10:
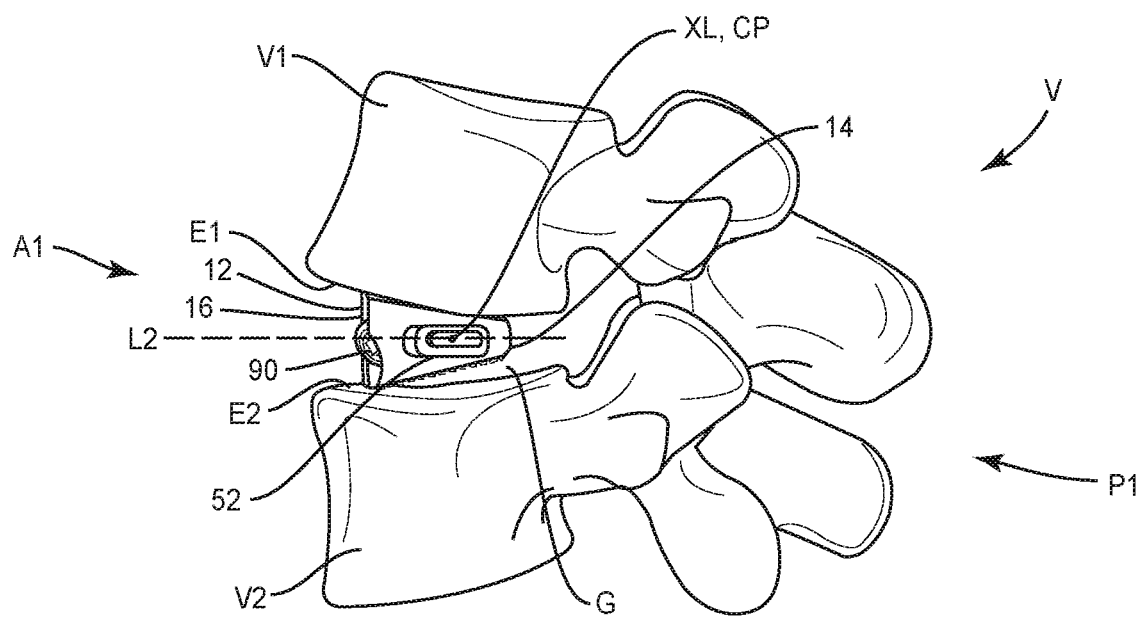
FIG. 10 is a side view of components of one embodiment of a surgical system in accordance with the principles of the present disclosure disposed with vertebrae.
Figure 14:
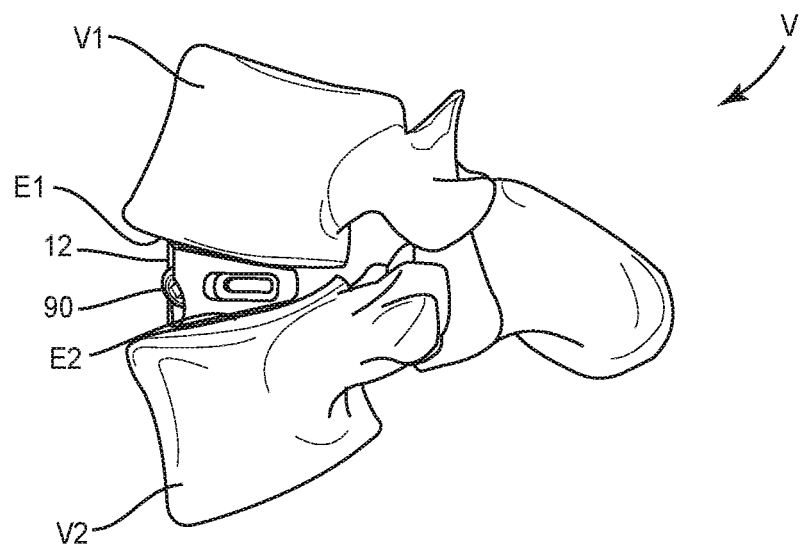
FIG. 14 is a side view of components of one embodiment of a surgical system in accordance with the principles of the present disclosure disposed with vertebrae.

Cage 12 includes a vertebral engaging surface 22 and a vertebral engaging surface 24. Surface 22 may be substantially planar and configured to engage endplate tissue of a vertebral body, such as, for example, an endplate E1 of a vertebral level V1 (FIG. 10). Surface 24 may be substantially planar and configured to engage endplate tissue of a vertebral body, such as, for example, an endplate E2 of a vertebral level V2 (FIG. 14). In some embodiments, surface 22 and/or surface 24 may be rough, textured, porous, semi-porous, dimpled, knurled, toothed, grooved and/or polished to facilitate engagement with tissue.

In some embodiments, surface 22 and/or surface 24 may be partially convex along axis L1 and/or at least partially convex in a direction substantially perpendicular to an axis L2 (i.e., from surface 16 to surface 14). In some embodiments, surface 22 and/or surface 24 may be angled along axis L1 or angled perpendicular to axis L1 such that anterior surface 16 is taller than posterior surface 14 such that cage 12 may be capable of creating and/or augmenting lateral or lordotic curvature in a spine when implanted. In some embodiments, vertebral tissue includes intervertebral tissue, endplate surfaces and/or cortical bone. In some embodiments, surface 22 and/or surface 24 may be coated with materials suitable for facilitating or encouraging bony ongrowth or fusion including but not limited to titanium and HA coatings. In some embodiments, a titanium coating is applied to surface 22 and/or surface 24 in a porous layer using plasma spray technology.

Cage 12 has a substantially rectangular configuration and includes an inner surface 26 and an outer surface 28. Surface 26 defines an opening 30 configured to receive an agent, which may include bone graft (not shown) and/or other materials, as described herein, for employment in a fixation or fusion treatment. In some embodiments, a plan geometry of cage 12 may have various configurations, such as, for example, oval, round, cylindrical, oblong, triangular, rectangular, polygonal having planar or arcuate side portions, irregular, uniform, non-uniform, consistent, variable, horseshoe shape, U-shape or kidney bean shape.

Cage 12 includes a surface 27 that defines an opening, such as, for example, a screw hole 42. Screw hole 42 extends through cage 12 in a transverse configuration relative to surfaces 22, 24, as described herein, for fixation with tissue. In some embodiments, surface 27 defines a fastener opening that is substantially smooth. In some embodiments, surface 27 defines one or a plurality of openings, each configured for disposal of a fastener.

Screw hole 42 defines an axis X1 oriented oblique relative to axis L1. Axis X1 is disposed at an oblique angle α1 relative to axis L1, as shown in FIG. 2. In some embodiments, angle α1 is in a range of approximately 0-60 degrees. In some embodiments, cage 12 is selectively disposed with vertebral tissue, as described herein, such that screw hole 42 is substantially aligned with an oblique surgical pathway P formed in subject body B, as shown in FIG. 8 and as described herein. For example, a surgical pathway P, as shown in FIG. 8, can be oriented oblique relative to a lateral axis XL of subject body B. In some embodiments, surgical pathway P is disposed at an oblique angle α relative to axis XL. In some embodiments, angle α is in a range of approximately 0-60 degrees. In some embodiments, substantial alignment of all or only a portion of screw hole 42 with all or only a portion of surgical pathway P includes co-axial, spaced apart, offset, angularly offset and/or parallel alignment.

In some embodiments, axis X1 is oriented oblique relative to axis XL such that screw hole 42 implants a spinal implant, such as, for example, a bone fastener 90, as described herein, oblique relative to axis XL. In some embodiments, axis XL lies in a coronal plane CP defined by subject body B. In some embodiments, cage 12 is selectively disposed with vertebral tissue, as described herein, such that screw hole 42 is substantially aligned with an oblique surgical pathway P relative to axis XL at an oblique angle α, which is equivalent to angle α1. In some embodiments, angle α is oriented approximately 0-60 degrees relative to axis XL such that bone fastener 90 is delivered via surgical pathway P to screw hole 42. In some embodiments, screw hole 42 is disposed at an angular orientation relative to plane CP and/or axis XL such that bone fastener 90 is delivered to a surgical site including an intervertebral space of one or more of the L2-L5 vertebral levels via surgical pathway P and oriented to penetrate endplate tissue of a vertebral body, such as, for example, endplate E1. In some embodiments, screw hole 42 and/or cage 12 may be disposed at an angular orientation relative to plane CP and/or axis XL such that bone fastener 90 is oriented to penetrate endplate tissue of a vertebral body.

Surface 28 includes an oblique surface 44 that defines a cavity, such as, for example, a counter bore 46 disposed in communication and alignment with screw hole 42. Oblique surface 44 is oriented with cage 12 and in substantial alignment with axis X1. In some embodiments, counter bore 46 is configured to guide bone fastener 90 into screw hole 42 relative to axis XL and in substantial alignment with surgical pathway P. In some embodiments, surface 44 and/or counter bore 46 includes a countersunk for disposal of a head of bone fastener 90.

Cage 12 includes a surface 49 that defines a cavity, such as, for example, an elongated opening 50. Surface 49 includes a track 52 that extends within opening 50 and is configured for engagement with a member 54. The portions of surface 49 that define opening 50 include walls configured to retain member 54 with cage 12 for slidable movement of member 54 relative to cage 12. Track 52 is disposed with opening 50 to define a track pathway 56 that facilitates translation of member 54 therein. Track pathway 56 extends substantially along axis L2 and transverse to axis L1. Track pathway 56 includes a limit, such as, for example, a lateral limit 58 and a limit, such as, for example, an oblique limit

60. Limits 58, 60 provide a range of translation of member 54 relative to cage 12 along track pathway 56, as described herein.

Member 54 is slidably engageable with track 52 for translation relative to cage 12 along track pathway 56. In some embodiments, member 54 is movable along track pathway 56 for translation substantially along axis L2 and/or transverse to axis L1. In some embodiments, member 54 is movable along track pathway 56 for rotation about axis L2 and/or axis L1. In some embodiments, track pathway 56 includes an arcuate configuration. In some embodiments, track pathway 56 extends along an arcuate configuration that is substantially concentric with track 52 and/or a lateral surface of cage 12. In some embodiments, track 52, surface 44 and/or track pathway 56 may be arcuate with a single radius defining an arcuate configuration. In some embodiments, track 52, surface 44 and/or track pathway 56 may be arcuate with multiple radii defining one or more portions of an arcuate configuration.

In some embodiments, track 52, surface 44 and/or track pathway 56 may extend along a pathway having various configurations corresponding to an overall shape of cage 12, such as, for example, round, cylindrical, oblong, triangular, rectangular, polygonal having planar or arcuate side portions, irregular, uniform, non-uniform, consistent, variable, horseshoe shape, U-shape or kidney bean shape. In some embodiments, surface 49 may be rough, textured, porous, semi-porous, dimpled, knurled, toothed, grooved and/or polished for selective translation of member 54.

Figure 3:
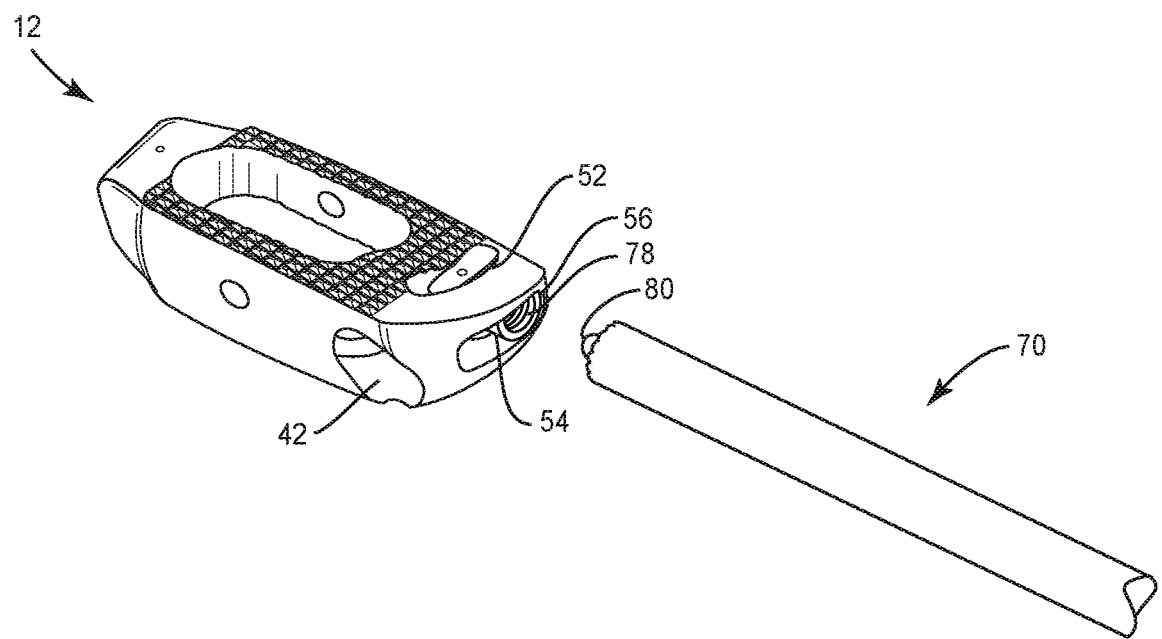
FIG. 3 is a perspective view of components of one embodiment of a surgical system in accordance with the principles of the present disclosure.
Figure 4:
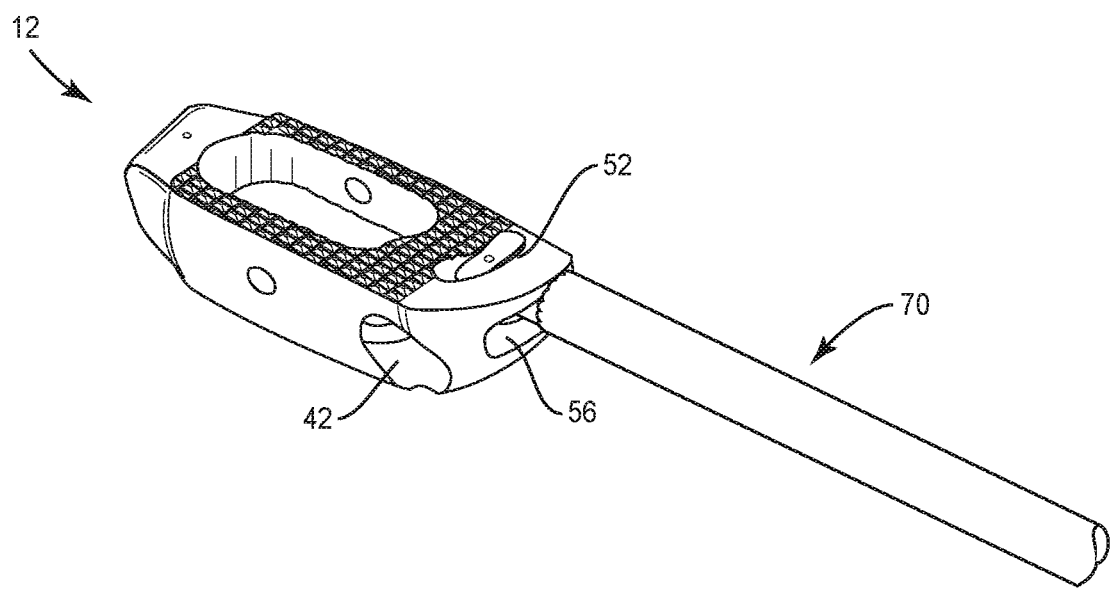
FIG. 4 is a perspective view of the components shown in FIG. 3.

In some embodiments, as shown in FIGS. 3 and 4, member 54 is retained with cage 12, as described herein, and configured for mating engagement with a surgical instrument, such as, for example, an inserter 70 described herein, to deliver cage 12 adjacent a surgical site via surgical pathway P, as described herein. For example, member 54 is configured to connect inserter 70 with cage 12 via opening 50 disposed with a lateral surface of cage 12. Member 54 includes a connecting surface 76 that defines a socket 78. Socket 78 is configured for releasable engagement with a portion 80 of inserter 70. In some embodiments, member 54 is freely translatable in situ within subject body B. In some embodiments, member 54 is positioned within subject body B and locked into a fixed position with inserter 70. In some embodiments, socket 78 and portion 80 can be configured for threaded engagement.

In some embodiments, inserter 70 is connected with member 54 and member 54 is translatable along track 52 and track pathway 56 relative to subject body B and/or cage 12 to provide selective positioning of cage 12 with respect to a patient's body for adapting to the configuration of the tissue surfaces of vertebrae. In some embodiments, oblique axis O (FIG. 8) includes any axis extending outward from an oblique surface (for example, surface 44 described herein) of cage 12 between lateral limit 58 and oblique limit 60, including but not limited to axes that are co-axial with axis L1 and/or an axis defined by surgical pathway P.

Spinal implant system 10 includes one or more bone fasteners 90 depending on the configuration of cage 12. In some embodiments, one or more of bone fasteners 90 may comprise multi-axial screws, sagittal angulation screws, pedicle screws, mono-axial screws, uni-planar screws, facet screws, fixed screws, tissue penetrating screws, conventional screws, expanding screws, wedges, anchors, buttons, dips, snaps, friction fittings, compressive fittings, expanding rivets, staples, nails, adhesives, posts, fixation plates and/or posts.

Bone fastener 90 includes a portion, such as, for example, a head 92 and a portion, such as, for example, an elongated shaft 94 configured for penetrating tissue. Head 92 includes an engagement portion configured for engagement with a surgical instrument. Shaft 94 has a cylindrical cross section configuration and includes an outer surface having an external thread form. In some embodiments, the external thread form may include a single thread turn or a plurality of discrete threads. In some embodiments, other engaging structures may be located on shaft 94, such as, for example, a nail configuration, barbs, expanding elements, raised elements and/or spikes to facilitate engagement of shaft 94 with tissue, such as, for example, vertebrae.

In some embodiments, all or only a portion of shaft 94 may have alternate cross section configurations, such as, for example, oval, oblong, triangular, square, polygonal, irregular, uniform, non-uniform, offset, staggered, undulating, arcuate, variable and/or tapered. In some embodiments, the outer surface of shaft 94 may include one or a plurality of openings. In some embodiments, all or only a portion of the outer surface of shaft 94 may have alternate surface configurations, such as, for example, smooth and/or surface configurations to enhance fixation with tissue, such as, for example, rough, arcuate, undulating, porous, semi-porous, dimpled, polished and/or textured. In some embodiments, all or only a portion of shaft 94 may be cannulated.

In some embodiments, spinal implant system 10 may comprise various surgical instruments, such as, for example, drivers, extenders, reducers, spreaders, distracters, blades, damps, forceps, elevators and drills, which may be alternately sized and dimensioned, and arranged as a kit. In some embodiments, spinal implant system 10 may comprise the use of microsurgical and image guided technologies, such as, for example, surgical navigation components employing emitters and sensors, which may be employed to track introduction and/or delivery of the components of spinal implant system 10 including the surgical instruments to a surgical site. See, for example, the surgical navigation components and their use as described in U.S. Pat. Nos. 6,021,343, 6,725,080, 6,796,988, the entire contents of each of these references being incorporated by reference herein.

Figure 5:
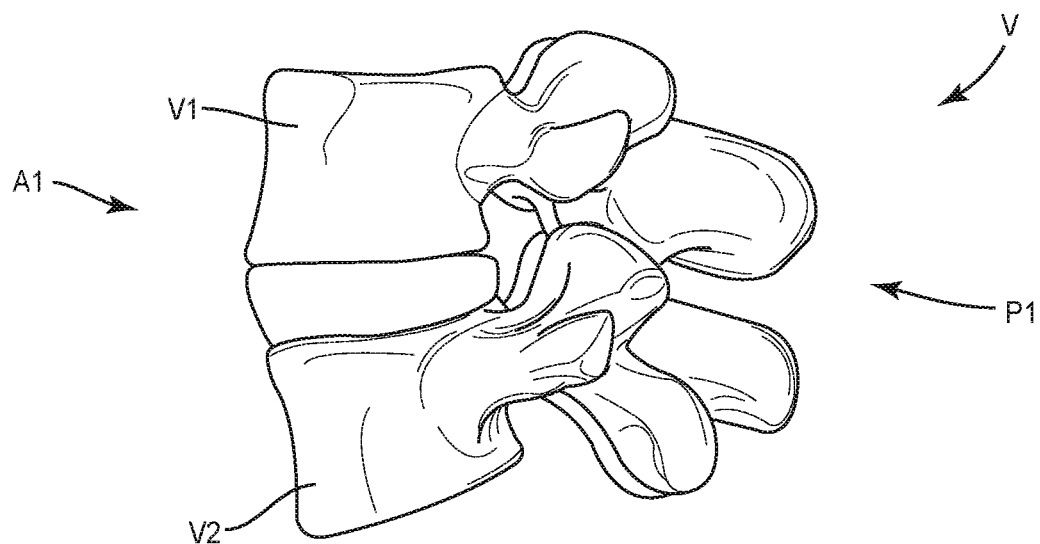
FIG. 5 is a side view of vertebrae.
Figure 6:
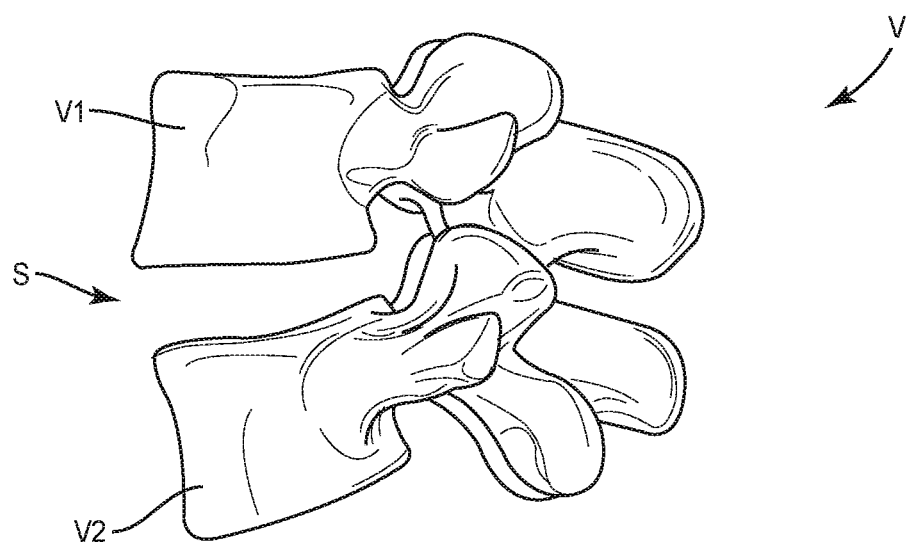
FIG. 6 is a side view of vertebrae.
Figure 7:
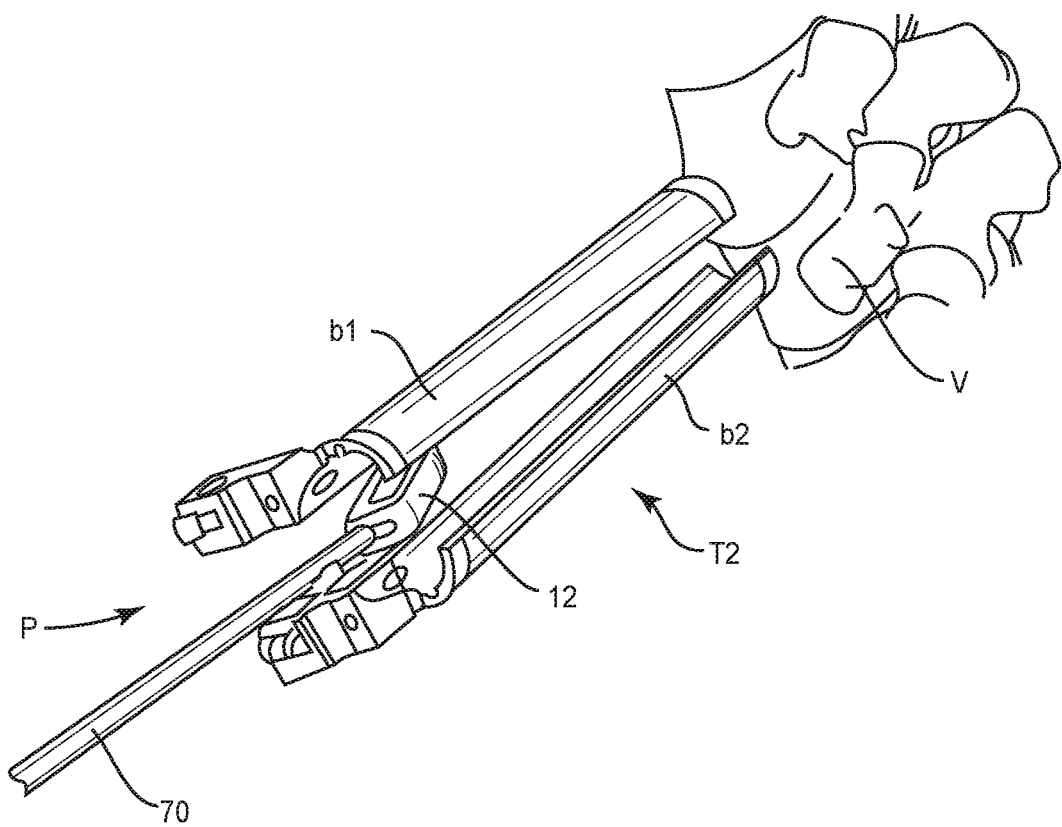
FIG. 7 is a perspective view of components of one embodiment of a surgical system in accordance with the principles of the present disclosure disposed with vertebrae.

In assembly, operation and use, as shown in FIGS. 5-16, spinal implant system 10, similar to the systems and methods described herein, is employed with a surgical procedure for treatment of a spinal disorder, such as those described herein, affecting a section of a spine of a patient. Spinal implant system 10 may also be employed with other surgical procedures to treat the affected section of vertebrae V of a patient utilizing a surgical procedure, such as, for example, an OLIF and DLIF procedure. In some embodiments, spinal implant system 10 may include retractors constrained via frame or semi-constrained using elastic or partial frame. In some embodiments, a surgical instrument, such as, for example, a retractor T2 is disposed in communication with surgical pathway P, disposed relative to axis XL at an oblique angle α, as described herein, for spacing tissue, as shown in FIG. 7. Retractor blades b1, b2 are inserted simultaneously as part of a unitary retractor instrument around one or more intervertebral spaces to protect vessels.

In some embodiments, as shown in FIGS. 5 and 6, an annulotomy and/or discectomy is performed with a surgical instrument (not shown) with x-ray confirmation of the starting point that is central on one or more intervertebral spaces. In some embodiments, spinal implant system 10 includes a semi-constrained retractor that facilitates minimal tissue pressures on surrounding abdominal structures and provides flexibility such that its blades rotate on a fixed pin allowing greater degrees of freedom of movement and working angles for a practitioner.

In some embodiments, a probe is passed into a disc space to secure its location. In some embodiments, the oblique angle and lordotic angle of the probe as it enters the disc space is assessed preoperatively and measured intraoperative using image guidance or using a mechanical or digital protractor. Fluoroscopy, image guidance and/or surgical navigation, as described herein, are used to confirm proper probe alignment into the disc space. In some embodiments, a guide wire is placed through a cannula into the disc space and positioning is confirmed with fluoroscopy. Instruments, such as, for example, a Cobb, mallet, shaver, serrated curettes, rasp, a ring curette, a uterine curette and/or combo tools are utilized to perform a discectomy of a disc space. The instruments enter subject body B obliquely through retractor T2 and can be turned orthogonally to allow the surgeon to work orthogonally across the disc space. The disc space is distracted until adequate disc space height is obtained, as shown in FIG. 6.

In some embodiments, cage 12 is configured for insertion within an intervertebral space S. In some embodiments, trial implants are delivered along surgical pathway P and used to distract one or more intervertebral spaces and apply appropriate tension in the intervertebral space allowing for indirect decompression. In some embodiments, a direct decompression of the disc space is performed by removing a portion of a herniated disc. In some embodiments, the size of cage 12 is selected after trialing, cage 12 is visualized by fluoroscopy and oriented before malleting into space S. Trialing is utilized to establish a starting point for cage 12 insertion. In some embodiments, an anterior longitudinal ligament (ALL) release procedure can be performed using an OLIF or a DLIF approach post-discectomy. For example, loosening the ALL can be performed by placing holes or partial cuts in the ALL such that the OLIF surgical pathway is immediately closer to the ALL. A pilot hole or the like is made in vertebra V1 adjacent space S, via surgical pathway P, for receiving bone fastener 90.

Figure 9:
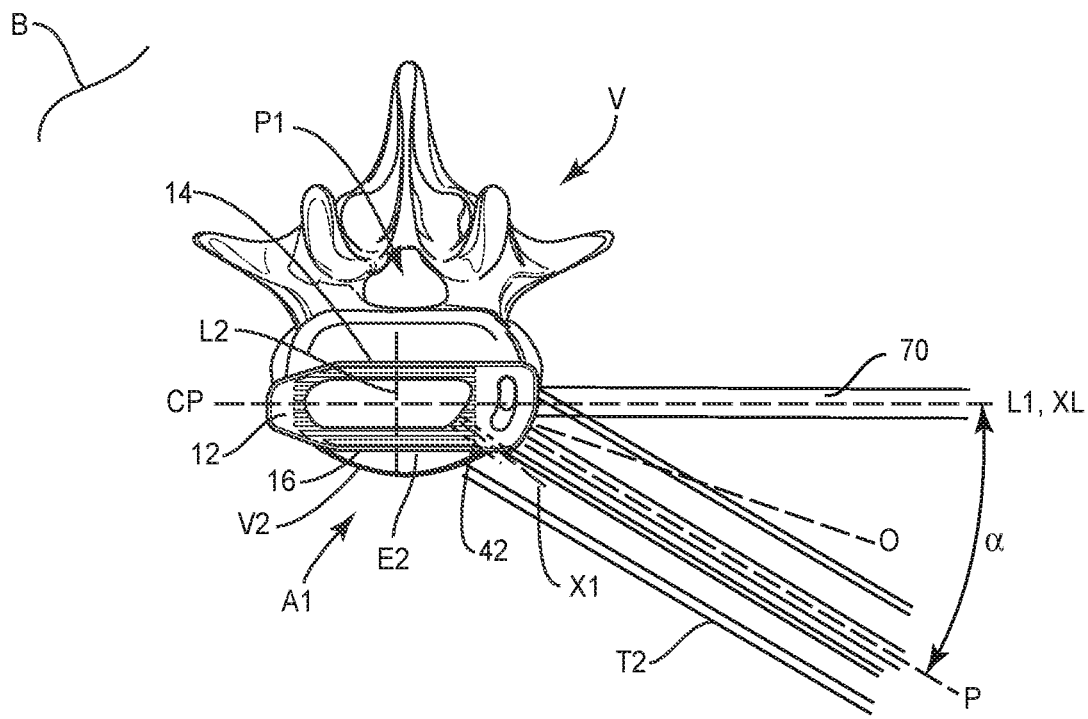
FIG. 9 is an axial view of components of one embodiment of a surgical system in accordance with the principles of the present disclosure disposed with vertebrae.

Cage 12 including member 54, as described herein, allows a surgeon to manipulate the cage 12 construct relative to retractor T2. For example, as shown in FIGS. 7-9, inserter 70 is connected with member 54 such that portion 80 engages socket 78. Inserter 70 is translatable with member 54 between limits 58, 60, as described herein, to facilitate insertion of cage 12 along surgical pathway P into position between vertebra V1 and vertebra V2 relative to subject body B and/or cage 12 to provide selective positioning of cage 12 with respect to subject body B for adapting to the configuration of the tissue surfaces of vertebrae V.

Inserter 70 and cage 12 are inserted along surgical pathway P substantially between blades b1, b2 of retractor T2, as shown in FIG. 7. The surgeon may freely rotate inserter 70 and cage 12 into position relative to vertebrae V1, V2. After positioning cage 12, the surgeon may utilize inserter 70, connected with member 54, to rotate cage 12 into position within space S to obtain a selected position of cage 12 relative to vertebrae V1, V2.

Figure 11:
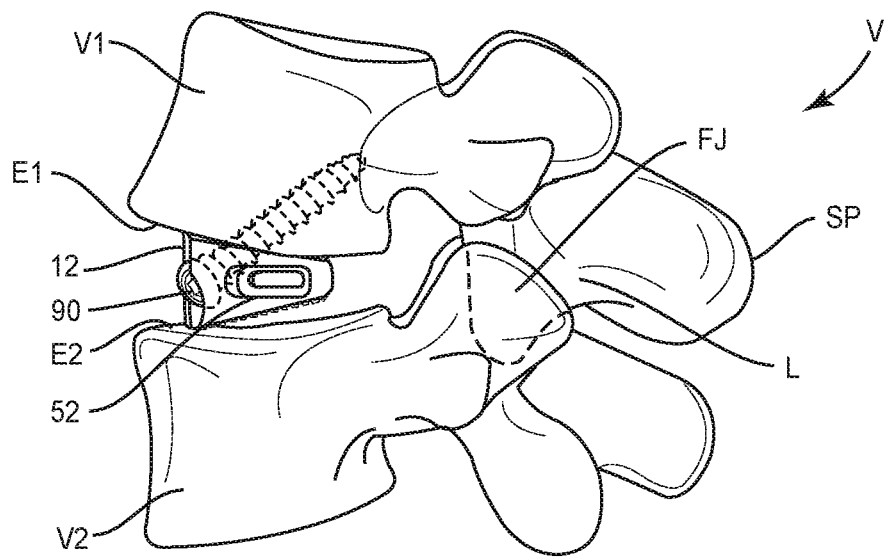
FIG. 11 is a side view, in part phantom, of components of one embodiment of a surgical system in accordance with the principles of the present disclosure disposed with vertebrae.

Inserter 70 orients cage 12 such that screw hole 42 is aligned oblique relative to axis XL. In some embodiments, cage 12 is selectively disposed with vertebrae V1, V2 such that screw hole 42 is substantially aligned with surgical pathway P relative to axis XL at angle α, which is equivalent to angle α1. Inserter 70 orients cage 12 such that surface 22 contacts and is disposed in flush engagement with an endplate E1 of vertebra V1, as shown in FIG. 10. Surface 22 engages endplate E1 such that cage 12 defines a gap G between surface 24 and an endplate E2 of vertebra V2. Bone fastener 90 is disposed with screw hole 42 and engaged in fixation with vertebra V1 such that bone fastener 90 is oriented oblique relative to lateral axis XL, as shown in FIG. 11. In some embodiments, cage 12 includes an alternately configured screw hole and/or is oriented with vertebrae V1, V2 such that bone fastener 90 is engaged in fixation with vertebra V2 such that bone fastener 90 is oriented oblique relative to lateral axis XL. In some embodiments, cage 12 includes a plurality of screw holes for disposal of bone fasteners 90 that are engaged in fixation with vertebra V1 and/or vertebra V2 in an oblique orientation relative to lateral axis XL.

Figure 12:
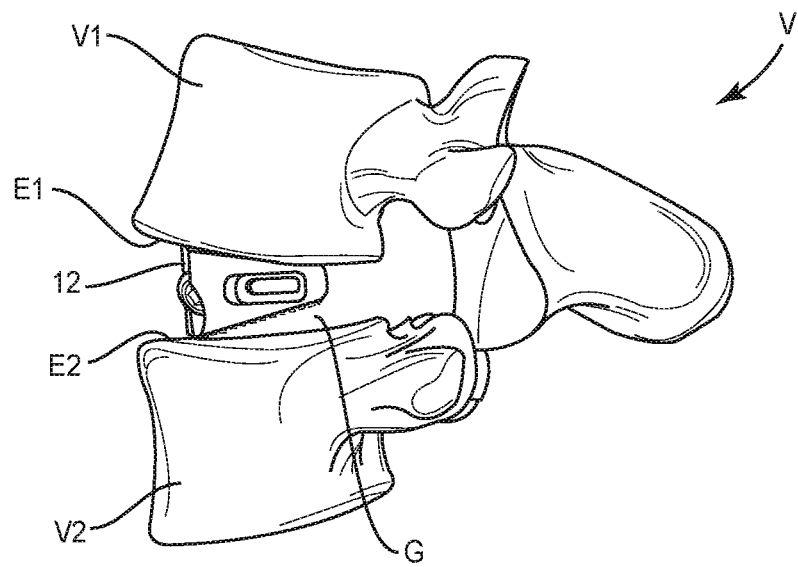
FIG. 12 is a side view of components of one embodiment of a surgical system in accordance with the principles of the present disclosure disposed with vertebrae.
Figure 13:
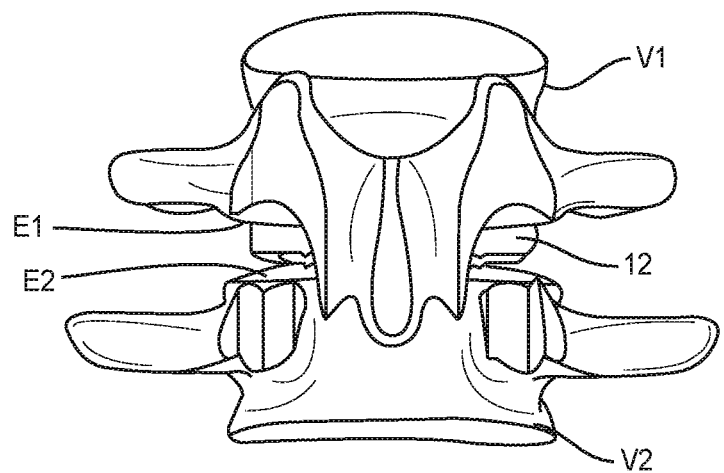
FIG. 13 is a plan view of components of one embodiment of a surgical system in accordance with the principles of the present disclosure disposed with vertebrae.
Figure 15:
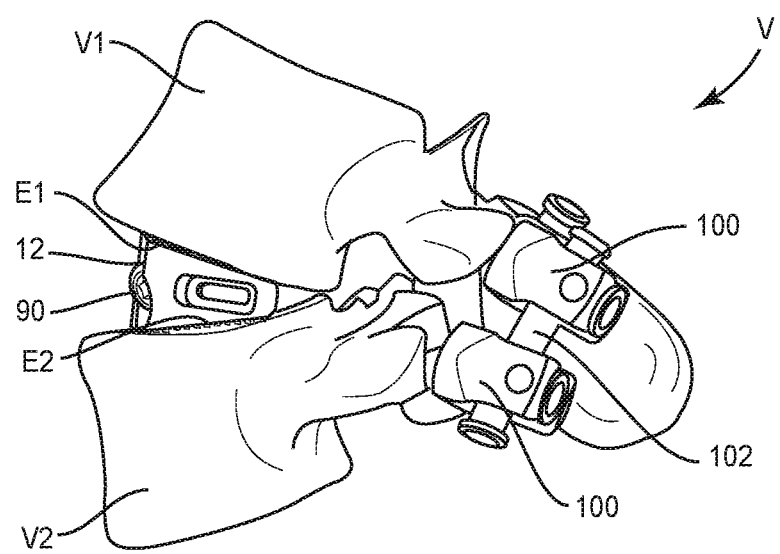
FIG. 15 is a side view of components of one embodiment of a surgical system in accordance with the principles of the present disclosure disposed with vertebrae.
Figure 16:
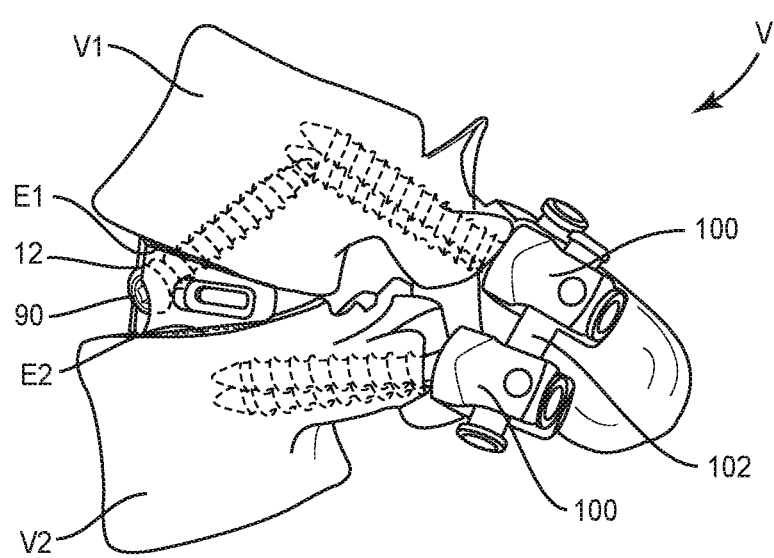
FIG. 16 is a side view, in part phantom, of components of one embodiment of a system in accordance with the principles of the present disclosure disposed with vertebrae.

In some embodiments, after fixation of cage 12 with vertebra V1, portions of facet joints FJ, laminae L and/or spinous process SP are removed to facilitate selected angular correction of vertebrae V, as shown in FIGS. 12 and 13, with surgical instruments, external manipulation of subject body B and/or posterior fixation devices such as pedicle screws attached with vertebrae V1, V2. For example, implant supports, such as, for example, extenders can be attached to the pedicle screws attached with vertebrae V1, V2. The extenders/screws act as levers for reducing and/or rotating vertebrae V to reduce and/or eliminate gap G and/or until endplate E2 is disposed in flush engagement with surface 24 such that a selected angular correction of vertebrae V is achieved, as shown in FIG. 14. In some embodiments, the components of spinal implant system 10 provide axial compression or distraction to restore vertebral body height, achieve lordosis and/or restore curvature of the spine. In some embodiments, a spinal construct including pedicle screws 100 and/or spinal rods 102, as shown in FIGS. 15 and 16, are employed to provide posterior fixation of vertebrae V1 V2 in a selected orientation and/or angular correction.

Upon completion of a procedure, as described herein, the surgical instruments, assemblies and non-implanted components of spinal implant system 10 are removed and the incision(s) are closed. One or more of the components of spinal implant system 10 can be made of radiolucent materials such as polymers. Radiopaque markers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal implant system 10. In some embodiments, spinal implant system 10 may include one or a plurality of plates, connectors and/or bone fasteners for use with a single vertebral level or a plurality of vertebral levels.

In some embodiments, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the components and/or surfaces of spinal implant system 10 with vertebrae. In some embodiments, the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal implant comprising:
an implant body extending between an anterior surface and a posterior surface, and including a first vertebral engaging surface and a second vertebral engaging surface, the implant body further including an inner surface that defines at least one opening oriented to implant a fastener oblique relative to a lateral axis of a subject body and adjacent an intervertebral space of the subject body, and
the implant body defining a cavity such that a surgical instrument is connectable with the implant body adjacent the cavity and movable relative to the implant body,
wherein the cavity includes a track pathway.

2. A spinal implant as recited in claim 1, further comprising a member movable in the cavity and connected with the surgical instrument.

3. A spinal implant as recited in claim 2, wherein the cavity includes an elongated opening configured for rotation of the member about a longitudinal axis of a subject body.

4. A spinal implant as recited in claim 1, wherein the cavity includes an arcuate configuration.

5. A spinal implant as recited in claim 1, wherein the at least one opening defines a longitudinal axis disposed at an oblique angle relative to the lateral axis.

6. A spinal implant as recited in claim 5, wherein the oblique angle is in a range of approximately 0-60 degrees.

7. A spinal implant as recited in claim 1, wherein the at least one opening is configured for alignment with an oblique surgical pathway.

8. A spinal implant as recited in claim 1, wherein the inner surface includes a first end and a second end that define a range of movement in the track pathway.

9. A spinal implant as recited in claim 1, wherein the implant body includes a lateral surface that defines an opening that communicates with the cavity.

10. A spinal implant as recited claim 1, further comprising a member movable in the cavity and including a socket configured for attachment with the surgical instrument.

11. A spinal implant as recited in claim 1, wherein the track pathway extends substantially along the lateral axis.

12. A spinal implant as recited in claim 1, further comprising a member movable in the cavity and connected with the surgical instrument, wherein portions of a surface that defines the cavity include walls configured to retain the member for slidable movement of the member relative to the implant body.

13. A method for treating a spine, the method comprising the steps of:
connecting a surgical instrument with an implant body adjacent a cavity of the implant body, the surgical instrument being movable relative to the implant body;
disposing the implant body between a first vertebral surface and a second vertebral surface of a subject body;
connecting the implant body with a first vertebral surface via a fastener disposed with at least one oblique opening of the implant body such that the implant body is disposed in flush engagement with the first vertebral surface; and
manipulating the subject body such that the second vertebral surface is selectively positioned with the implant body.

14. A method as recited in claim 13, further comprising the step of fixing the vertebral surfaces in the selected angular orientation.

15. A method as recited in claim 14, wherein the step of fixing includes posterior fixation of the vertebral surfaces.

16. A method as recited in claim 13, wherein the step of manipulating includes rotating the first vertebral surface and/or the second vertebral surface such that the implant body is disposed in flush engagement with the second vertebral surface.

17. A method as recited in claim 13, wherein the step of manipulating includes rotating the first vertebral surface to a selected angular orientation relative to the second vertebral surface.

18. A spinal implant system comprising:
an implant body extending between an anterior surface and a posterior surface, and including a first vertebral engaging surface and a second vertebral engaging surface, the implant body further including an inner surface that defines at least one opening oriented oblique relative to a lateral axis of a subject body, the implant body defining a cavity;
a bone fastener disposable with the at least one opening; and
a surgical instrument connectable with the implant body adjacent the cavity and movable relative to the implant body,
wherein the at least one opening includes a single screw hole.

19. A spinal implant system as recited in claim 18, wherein the cavity includes a track and further comprising a member movable along the track.

20. A spinal implant system as recited in claim 18, wherein the at least one opening is disposed at an angle of approximately 0-60 degrees relative to the lateral axis and substantially aligned with an oblique surgical pathway such that the at least one opening is configured to receive the bone fastener via the oblique surgical pathway.

* * * * *

UNITED STATES PATENT AND TRADEMARK OFFICE
CERTIFICATE OF CORRECTION

PATENT NO. : 9,895,235 B2  
APPLICATION NO. : 14/974685  
DATED : February 20, 2018  
INVENTOR(S) : Melkent et al.

Page 1 of 1

It is certified that error appears in the above-identified patent and that said Letters Patent is hereby corrected as shown below:

In the Specification

In Column 6, Line 54, delete "OLIF procedure." and insert -- DLIF procedure. --, therefor.

In Column 10, Line 29, delete "distracters," and insert -- distractors, --, therefor.

In Column 12, Line 35, delete "V1 V2" and insert -- V1, V2 --, therefor.

In the Claims

In Column 13, Line 38, in Claim 10, delete "recited claim" and insert -- recited in claim --, therefor.

Signed and Sealed this  
Tenth Day of July, 2018

Andrei Iancu  
*Director of the United States Patent and Trademark Office*